(12) United States Patent
Matsumoto et al.

(10) Patent No.: US 7,071,349 B2
(45) Date of Patent: Jul. 4, 2006

(54) PURIFICATION METHOD OF N-(1(S)-ETHOXYCARBONYL-3-PHENYL PROPYL)-L-ALANINE

(75) Inventors: Akira Matsumoto, Iruma-gun (JP); Michio Nomura, Kakogawa (JP); Yoshikazu Kogame, Himeji (JP); Yasuyoshi Ueda, Himeji (JP)

(73) Assignee: Kanaka Corporation, Osaka (JP)

( * ) Notice: Subject to any disclaimer, the term of this patent is extended or adjusted under 35 U.S.C. 154(b) by 0 days.

(21) Appl. No.: 10/311,060

(22) PCT Filed: Mar. 19, 2002

(86) PCT No.: PCT/JP02/02570

§ 371 (c)(1),
(2), (4) Date: Apr. 8, 2003

(87) PCT Pub. No.: WO02/074728

PCT Pub. Date: Sep. 26, 2002

(65) Prior Publication Data

US 2003/0162991 A1   Aug. 28, 2003

(30) Foreign Application Priority Data

Mar. 19, 2001   (JP) ............................. 2001-078695

(51) Int. Cl.
*C07C 229/00* (2006.01)

(52) U.S. Cl. ..................................... 560/38
(58) Field of Classification Search .............. 560/16, 560/29, 33, 159, 160, 38
See application file for complete search history.

(56) References Cited

U.S. PATENT DOCUMENTS

| 4,808,741 A | 2/1989 | Oudenes |
| 5,387,696 A | 2/1995 | Kottenhalm et al. |
| 5,756,812 A | 5/1998 | Hackl et al. |
| 6,118,010 A * | 9/2000 | Ueda et al. ............... 548/532 |

FOREIGN PATENT DOCUMENTS

| EP | 190687 A1 | 8/1986 |
| JP | 58-103364 A | 6/1983 |
| JP | 59-181247 A | 10/1984 |
| JP | 63-174956 A | 7/1988 |
| JP | 64-45348 A | 2/1989 |
| JP | 64-45350 A | 2/1989 |
| JP | 3-22867 B2 | 3/1991 |
| JP | 5-201882 A | 8/1993 |
| JP | 9-301938 A | 11/1997 |

OTHER PUBLICATIONS

International Search Report for PCT/JP02/02570 dated Jul. 2, 2002.

* cited by examiner

*Primary Examiner*—Cecilia J. Tsang
*Assistant Examiner*—Taylor Victor Oh
(74) *Attorney, Agent, or Firm*—Sughrue Mion, PLLC

(57) ABSTRACT

The present invention is to provide a purification method of obtaining N-(1(S)-ethoxycarbonyl-3-phenylpropyl)-L-alanine of high quality in good yield with high productivity, which is accordingly suited for commercial scale application.

An impurity-contaminated N-(1(S)-ethoxycarbonyl-3-phenylpropyl)-L-alanine is crystallized from a mixed solvent of alcohol and water in a volume ratio of alcohol/water being 1 to 20 to remove a contaminating impurity into a mother liquor and give crystals of N-(1(S)-ethoxycarbonyl-3-phenylpropyl)-L-alanine.

22 Claims, No Drawings

PURIFICATION METHOD OF N-(1(S)-ETHOXYCARBONYL-3-PHENYLPROPYL)-L-ALANINE

FIELD OF THE INVENTION

The present invention relates to a purification method of N-(1(S)-ethoxycarbonyl-3-phenylpropyl)-L-alanine represented by the following formula (1).

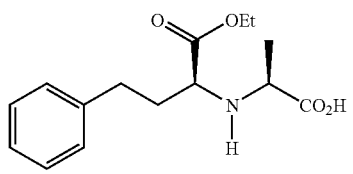

(1)

N-(1(S)-ethoxycarbonyl-3-phenylpropyl)-L-alanine is a compound of great use as an intermediate for the production of pharmaceuticals, particularly an intermediate for the production of several antihypertensive drugs (angiotension converting enzyme inhibitors) such as enalapril and ramipril.

PRIOR ART

The hithereto-known synthetic method of N-(1(S)-ethoxycarbonyl-3-phenylpropyl)-L-alanine includes:
(a) the process involving Michael addition reaction of L-alanine to ethyl β-benzoylacrylate and subsequent catalytic reduction for transformation of the carbonyl group of the benzoyl moiety to a methylene group (e.g. JP-A-03-22867)
(b) the process involving Michael addition reaction of L-alanine benzyl ester to ethyl β-benzoylacrylate and subsequent catalytic reduction for concurrent transformation of the carbonyl group of the benzoyl moiety to a methylene group and cleavage of the benzyl ester (e.g. JP-A-58-103364),
(c) the process which comprises reacting (S)-homophenylalanine ethyl ester with (S)- or (RS)-propionic acid having a leaving group (halogen atom, sulfonyloxy group, or the like) in the α-position (e.g. JP-A-63-174956),
(d) the process which comprises reacting (S)-homophenylalanine ethyl ester with (S)- or (RS)-propionic acid benzyl ester having a leaving group (halogen atom, sulfonyloxy group, or the like) in the α-position and then subjecting the reaction product to catalytic reduction for cleavage of the benzyl ester (e.g. JP-A-59-181247),
(e) the process which comprises reacting ethyl (R)- or (RS)-phenylbutyrate having a leaving group(halogen atom, sulfonyloxy group, or the like) in the α-position with L-alanine benzyl or t-butyl ester of and subjecting the reaction product to catalytic reduction or acid treatment for cleavage of said benzyl or t-butyl ester (Chem. Pharm. Bull. 37(2), 280, 1989), and
(f) the process which comprises subjecting ethyl 2-oxo-4-phenylbutyrate and L-alanine or L-alanine benzyl ester to reductive amination (e.g. JP-A-05-201882), etc.
In the above synthetic methods, production of the objective compound N-(1(S)-ethoxycarbonyl-3-phenylpropyl)-L-alanine is accompanied by formation or remaining of various structurally analogous impurities as byproducts or residual contaminants.

As such impurities, there can be mentioned optical isomers, namely N-(1(R)-ethoxycarbonyl-3-phenylpropyl)-L-alanine represented by the following formula (2),

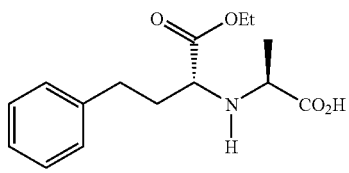

(2)

N-(1(S)-ethoxycarbonyl-3-phenylpropyl)-D-alanine represented by the following formula (3),

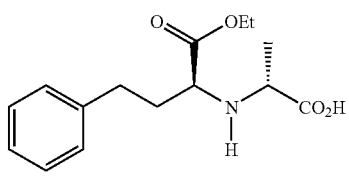

(3)

and N-(1(R)-ethoxycarbonyl-3-phenylpropyl)-D-alanine represented by the following formula (4);

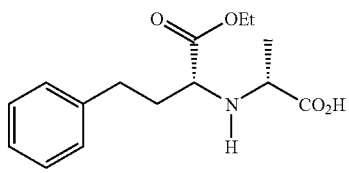

(4)

the cyclohexyl derivative, namely N-(1(S)-ethoxycarbonyl-3-cyclohexylpropyl)-L-alanine represented by the following formula (5);

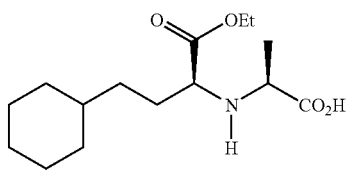

(5)

the carboxy derivative, namely N-(1(S)-carboxy-3-phenylpropyl)-L-alanine represented by the following formula (6);

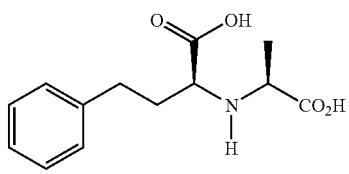

(6)

the ester derivatives, namely N-(1(S)-ethoxycarbonyl-3-phenylpropyl)-L-alanine ester represented by the following formula (7),

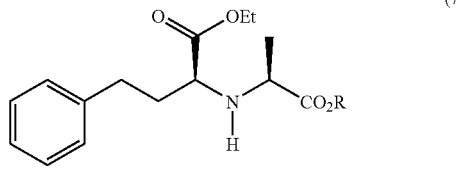

(7)

in the formula, R represents an alkyl group or an aralkyl group; and ethyl phenylbutyrate, etc.

The optical isomers are formed when the optical purity of the starting material is low, when the stereoselectivity of the reaction is insufficient, or due to racemization of the staring material or intermediate compound. Though it depends on the synthetic method, generally N-(1(R)ethoxycarbonyl-3-phenylpropyl)-L-alanine of the above formula (2) and N-(1(S)-ethoxycarbonyl-3-phenylpropyl)-D-alanine of the above formula (3) are formed as major byproducts.

The cyclohexyl derivative results from hydrogenation of the benzene ring in catalytic reduction. The carboxy derivative results from cleavage of an ester moiety in hydrolysis or catalytic reduction. The ester derivatives correspond to the compounds in which the terminal carboxyl groups of the objective compounds are esterified. The formation of the derivatives result from remaining of the starting material owing to incomplete reaction or some side reaction. Referring to the formula (7), R represents an alkyl group of 1 to 8 carbon atoms (particularly an alkyl group of 1 to 4 carbon atoms) such as ethyl, t-butyl or the like group or an aralkyl group of 7 to 10 carbon atoms such as benzyl or the like group. The ethyl phenylbutyrate results from reduction of ethyl β-benzoylacrylate.

Of course, contamination of the product (N-(1(S)-ethoxycarbonyl-3-phenylpropyl)-L-alanine) with such structurally analogous impurities should be avoided as far as possible and an effective purification technology is required for the purpose.

The hitherto-known purification method of N-(1(S)-ethoxycarbonyl-3-phenylpropyl)-L-alanine includes, for example:

(1) the method of removing said optical isomers, particularly the diastereomer (1S/1R ratio=95/5→1S/1R ratio=99/1) by crystallization from ethyl acetate. (JP-A-03-22867)
(2) the method of removing said carboxy derivative by crystallization from boiling water (AT402639B), etc.

Regarding the isolation method of N-(1(S)-ethoxycarbonyl-3-phenylpropyl)-L-alanine, for example JP-A-05-201882 describes a method which comprises crystallizing an evaporation residue of the extracted organic phase from chilled ethanol or acetone, but there is no description referring to the impurity-removing effect.

The present inventors made an investigation and as a result, they revealed that the above crystallization methods are not sufficient in impurity-removing effect as reported in the past (AT402639B, JP-A-09-301938, etc.). Thus, for example, crystallization from ethyl acetate may hardly remove said carboxy derivative, and crystallization from water may hardly remove said cyclohexyl derivative, ester derivative, and ethyl phenylbutyrate which has low polarity.

Furthermore, in the conventional purification method, the low solubility of N-(1(S)-ethoxycarbonyl-3-phenylpropyl)-L-alanine in water or a solvent such as ethanol makes it difficult to effect crystallization in a high concentration range, thus having a problem from the standpoint of productivity on a commercial scale. In addition, the physical properties (liquid behaviors) of the resulting crystal slurry and the physical properties (powder characteristics) of the resulting crystal cannot necessarily be said to be satisfactory, and there found problems such that the crystals cannot be easily discharged from the crystallization tank, are not easy to dry and tend to form cakes in the drying stage, and that because of small bulk specific gravity, containers of large capacity are required for packaging.

Thus, the conventional purification methods are not preferable enough from the standpoint of product purity, powder characteristics, yield, productivity and the like.

SUMMARY OF THE INVENTION

In view of the above state of art, the present invention has for its object to provide a purification method of obtaining N-(1(S)-ethoxycarbonyl-3-phenylpropyl)-L-alanine of high quality, namely of high purity and having favorable powder characteristics, in good yield with high productivity, which is accordingly suited for commercial scale application.

The present inventors made an intensive investigation for solving the above subject and as a result, found that carrying out crystallization by using a mixed solvent of alcohol and water provides for marked improvements in the solubility, impurity-removing effect, slurry behavior, and powder characteristics, all of which are parameters determinant of yield, quality, operability, and productivity. The present invention has accordingly been developed.

The present invention, therefore, is directed to a purification method of N-(1(S)-ethoxycarbonyl-3-phenylpropyl)-L-alanine represented by the formula (1)

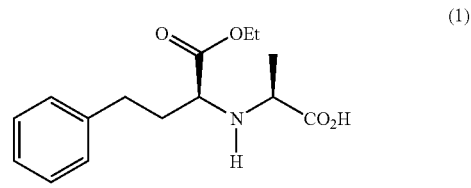

(1)

which comprises crystallizing impurity-contaminated N-(1(S)-ethoxycarbonyl-3-phenylpropyl)-L-alanine from a mixed solvent of alcohol and water in a volume ratio of alcohol/water being 1 to 20 to remove a contaminating impurity into a mother liquor and give crystals of N-(1(S)-ethoxycarbonyl-3-phenylpropyl)-L-alanine.

Moreover, the present invention is related to the above purification method wherein the contaminating impurity is at least one compound selected from the group consisting of N-(1(R)-ethoxycarbonyl-3-phenylpropyl)-L-alanine, N-(1(S)-ethoxycarbonyl-3-phenylpropyl)-D-alanine, N-(1(R)-ethoxycarbonyl-3-phenylpropyl)-D-alanine, N-(1(S)-ethoxycarbonyl-3-cyclohexylpropyl)-L-alanine, N-(1(S)-carboxy-3-phenylpropyl)-L-alanine, N-(1(S)-ethoxycarbonyl-3-phenylpropyl)-L-alanine ester, and ethyl phenylbutyrate.

Further, the present invention is related to the above purification method wherein the crystallization is carried out under forced fluidity with a condition of not less than 0.1 kW/m³; the above purification method wherein the crystallization is carried out at a temperature of not lower than 20° C.; the above purification method wherein the crystallization is carried out at a crystallizing speed of not more than 50% of a total crystal output/hour; the above purification method wherein the crystallization is carried out at pH 3 to 6; the above purification method wherein the crystallization is carried out by at least one of crystallization by cooling and crystallization by concentration; the above purification method wherein the crystallization is carried out by crystallization by cooling; and the above purification method wherein the cooling speed for the crystallization by cooling is not more than 40° C./hour.

Further, the present invention is related to the above purification method wherein the alcohol is a monohydric alcohol of 1 to 8 carbon atoms; the above purification method wherein the alcohol is a monohydric alcohol of 1 to 4 carbon atoms; the above purification method wherein the alcohol is ethanol; the above purification method wherein the ethanol is denatured with a denaturing agent other than alcohol; the purification method wherein a treatment with an adsorbent is carried out prior to the crystallization; and the above purification method wherein the adsorbent is active charcoal.

DETAILED DESCRIPTION OF THE INVENTION

The present invention is now described in detail.

In the present invention, for obtaining N-(1(S)-ethoxycarbonyl-3-phenylpropyl)-L-alanine of high quality, namely of high purity and having favorable powder characteristics, from impurity-contaminated N-(1(S)-ethoxycarbonyl-3-phenylpropyl)-L-alanine, in good yield with high productivity, the crystallization is carried out from a mixed solvent of alcohol and water.

The above alcohol is not particularly restricted and includes, for example, monohydric alcohols of 1 to 12 carbon atoms such as methanol, ethanol, 1-propanol, 2-propanol, 1-butanol, 2-butanol, isobutanol, t-butanol, 1-pentanol, 2-pentanol, 3-pentanol, 2-methyl-1-butanol, isopentyl alcohol, t-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 3,3,5-trimethyl-1-hexanol, 1-decanol, 1-undecanol, 1-dodecanol, allyl alcohol, propargyl alcohol, cyclohexanol, 1-methylcyclohexanol, 2-methylcyclohexanol, 3-methylcyclohexanol, 4-methylcyclohexanol, benzyl alcohol and so on.

Preferred are alcohols of 1 to 8 carbon atoms and include, for example, methanol, ethanol, 1-propanol, 2-propanol, 1-butanol, 2-butanol, isobutanol, t-butanol, 1-pentanol, 2-pentanol, 3-pentanol, 2-methyl-1-butanol, isopentyl alcohol, t-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, allyl alcohol, propargyl alcohol, cyclohexanol, 1-methylcyclohexanol, 2-methylcyclohexanol, 3-methylcyclohexanol, 4-methylcyclohexanol, benzyl alcohol, and so on.

From the standpoint of product quality, yield, and productivity, a monohydric alcohol of 1 to 6 carbon atoms is more preferred and there can be mentioned, for example, methanol, ethanol, 1-propanol, 2-propanol, 1-butanol, 2-butanol, isobutanol, t-butanol, 1-pentanol, 2-pentanol, 2-methyl-1-butanol, isopentyl alcohol, t-pentyl alcohol, 3-methyl-2-butanol, neopentyl alcohol, 1-hexanol, 2-methyl-1-pentanol, 4-methyl-2-pentanol, 2-ethyl-1-butanol, allyl alcohol, propargyl alcohol, cylohexanol, and so on.

The monohydric alcohol of 1 to 4 carbon atoms is still more preferred in that it can be appropriately heated for enhanced solubility, that both removal of the solvent from wet crystals and recovery of the solvent from the crystallization filtrate can be easily accomplished, that it is hardly solidified on cooling to a temperature below room temperature, that it is easy to work with because of its low viscosity, and that it is advantageous in terms of solvent cost and availability. For example, there can be mentioned methanol, ethanol, 1-propanol, 2-propanol, 1-butanol, 2-butanol, isobutanol, t-butanol, allyl alcohol, propargyl alcohol, and so on.

When any alcohol other than ethanol is used, depending on conditions, byproducts due to transesterification of N-(1(S)-ethoxycarbonyl-3-phenylpropyl)-L-alanine, which are hardly removed, tend to form (e.g. N-(1(S)-methoxycarbonyl-3-phenylpropyl)-L-alanine and N-(1(S)-methoxycarbonyl-3-phenylpropyl)-L-alanine methyl ester). Therefore, it is most preferable to use ethanol.

When ethanol is used, that ethanol may be denatured with a denaturing agent. Usable as the denaturing agent include isopropyl alcohol, methanol, ethyl acetate, methyl isobutyl ketone, aliphatic hydrocarbons (e.g. hexane and heptane), and aromatic hydrocarbons (e.g. toluene and benzene), and so forth. Among these, it is preferable to use a denaturing agent other than alcohols. More preferred are aliphatic hydrocarbons and aromatic hydrocarbons, with toluene being particularly preferred. The level of addition of the denaturing agent is generally not higher than 10% relative to the volume of ethanol.

In the present invention, as an auxiliary solvent, water is used in combination with said alcohol. Concomitant use of water increases the solubility of N-(1(S)-ethoxycarbonyl-3-phenylpropyl)-L-alanine to an appropriate level and leads to improvements not only in yield and productivity but also in impurity-removing effect, slurry behavior, and physical properties of crystals (powder characteristics).

The volume ratio of alcohol to water for crystallization depends on the kind of alcohol to be used but it is necessary that the alcohol/water volume ratio is 1 to 20. The upper limit is preferably 18, more preferably 16, still more preferably 14, particularly preferably 10. From quality points of view, it is more preferably 5, still more preferably 4, particularly preferably 3. The lower limit is preferably 1.5, more preferably 2, from quality points of view. The preferable range is 1.5 to 10, more preferably 2 to 5, still more preferably 2 to 4, particularly preferably 2 to 3 by which condition the crystallization can suitably be carried out. It is preferred that the ratio is selected so as to attain the yield of not less than about 70%, preferably not less than 80%, more preferably not less than 90%.

In the present invention, the crystallization of N-(1(S)-ethoxycarbonyl-3-phenylpropyl)-L-alanine is preferably carried out at pH 3 to 6, more preferably at pH 4 to 5 of the solution composed of the crystals and the above mixed solvent, from the standpoint of yield and quality (inclusive of inhibition of formation of byproduct impurities). When the pH of the solution is too low or too high owing to the presence of impurities and so on, the pH can be adjusted, for example, with an acid, such as hydrochloric acid or sulfuric acid, or an alkali, e.g. an alkali metal hydroxide, such as sodium hydroxide or lithium hydroxide.

In the present invention, the crystallization of N-(1(S)-ethoxycarbonyl-3-phenylpropyl)-L-alanine is preferably carried out under forced fluidity. From quality points of view, the fluidity in terms of agitation power per unit volume is preferably not less than about 0.1 kW/m$^3$, more preferably not less than about 0.2 kW/m$^3$, still more preferably not less than about 0.3 kW/m$^3$. The upper limit is not particularly restricted, but is preferably not higher than about 20 kW/m$^3$, more preferably not higher than about 10 kW/m$^3$. The forced fluidity mentioned above is generally established by rotation of a stirring impeller, but it is not always necessary to employ the stirring impeller provided that the above fluidity is obtained. For example, a system utilizing circulation of the solution can be exploited.

From quality (product purity, powder characteristics) points of view, the crystallization of N-(1(S)-ethoxycarbonyl-3-phenylpropyl)-L-alanine is preferably carried out under warming condition and is preferably carried out at a temperature of not lower than about 20° C., more preferably not lower than about 30° C. The upper limit is preferably not higher than about 80° C., more preferably not higher than about 70° C. The crystallization can suitably be carried out at about 20° to 80° C.

The crystallization according to the present invention can be carried out by the routine crystallizing technique, that is to say at least any one of such techniques as crystallization by cooling, crystallization by neutralization, and crystallization by concentration (inclusive of crystallization by solvent exchange). It is preferable to use at least one of crystallization by cooling and crystallization by concentration, and is particularly preferable to use crystallization by cooling.

To maximize the effect of the invention, it is preferable that the contamination of various impurities into crystals of N-(1(S)-ethoxycarbonyl-3-phenylpropyl)-L-alanine be minimized by controlling the crystallizing speed, that is to say the crystal output per unit period. The crystallizing speed is preferably not more than about 50% of the total crystal output/hour, more preferably not more than about 25% of the total crystal output/hour. The lower limit is preferably 1% of the total crystal output/hour, more preferably 2% of the total crystal output/hour.

In the case of crystallization by cooling, the cooling speed is preferably not more than about 40° C./hour, more preferably not more than about 20° C./hour, still more preferably not more than about 10° C./hour, particularly preferably not more than 5° C./hour, from quality points of view. The lower limit is preferably not less than about 1° C./hour, more preferably not less than about 2° C./hour. In this case, since abrupt crystallization with collapse of a large built-up of supersaturation is undesirable from quality points of view, it is good practice to add seed crystals to provide for smooth nucleation where necessary.

The crystal concentration at completion of crystallization is not particularly restricted and this is also dependent on the kind of alcohol to be used but the weight ratio of N-(1(S)-ethoxycarbonyl-3-phenylpropyl)-L-alanine relative to the volume of the solvent is preferably about 5 to 40 w/v %, more preferably about 10 to 35 w/v %, still more preferably 20 to 30 w/v %.

The purification method of the present invention provides for a high impurity-removing effect and is particularly effective in removing optical isomers (N-(1(R)-ethoxycarbonyl-3-phenylpropyl)-L-alanine, N-(1(S)-ethoxycarbonyl-3-phenylpropyl)-D-alanine and N-(1(R)-ethoxycarbonyl-3-phenylpropyl)-D-alanine), cyclohexyl derivative (N-(1(S)-ethoxycarbonyl-3-cyclohexylpropyl)-L-alanine), carboxy derivative (N-(1(S)-carboxy-3-phenylpropyl)-L-alanine), ester derivative (N-(1(S)-ethoxycarbonyl-3-phenylpropyl)-L-alanine ester), and ethyl phenylbutyrate. In particular, it is very effective in removing the cyclohexyl derivative which is otherwise extremely difficult to remove. Moreover, the technology is effective in removing iron and other inorganic contaminants as well.

To assist in impurity removal, it is effective to treat the substrate with an adsorbent, preferably with active charcoal, prior to the crystallization.

The crystals of N-(1(S)-ethoxycarbonyl-3-phenylpropyl)-L-alanine obtainable by the purification method of the invention can be obtained as wet crystals by the conventional solid-liquid separation/cake washing procedure (centrifugation, pressure filtration, suction filtration, etc.) and can also be obtained as dry crystals by subjecting the wet crystals further to the conventional drying procedure (e.g. air drying, drying under reduced pressure, drying in vacuo, etc.). In conducting the solid-liquid separation, the yield can be maximized by cooling the system to a temperature not higher than about 20° C., preferably 0 to 10° C.

Though not particularly restricted, the purification method of the invention can suitably be used as an isolation method or a recrystallization method for obtaining the crystals of N-(1(S)-ethoxycarbonyl-3-phenylpropyl)-L-alanine synthesized by any known production method mentioned above, particularly of N-(1(S)-ethoxycarbonyl-3-phenylpropyl)-L-alanine synthesized by the method involving Michael addition reaction as mentioned hereinbefore under (a) or (b) in Prior Art.

It is considered that the effect of the present invention results from the fact that water content inside the crystals is high when N-(1(S)-ethoxycarbonyl-3-phenylpropyl)-L-alanine is crystallized from the mixed solvent of alcohol and water comparing to when crystallized from alcohol.

BEST MODE FOR CARRYING OUT THE INVENTION

The following examples illustrate the present invention in further detail without defining the scope of the invention.

PRODUCTION EXAMPLE

Production of
N-(1-ethoxycarbonyl-3-phenylpropyl)-L-alanine

To a solution of 25.9 g of ethyl trans-β-benzoylacrylate in 770 ml of ethanol was added a solution of 6.03 g of L-alanine lithium salt in 426 ml of ethanol over 30 minutes at room temperature. After completion of addition, the mixture was stirred for an additional 5 minutes, and then 5.29 ml of concentrated hydrochloric acid was added, followed by cooling with ice-water. As seed crystals, 679 mg of N-(1(S)-ethoxycarbonyl-3-oxo-3-phenylpropyl)-L-alanine was added, and the mixture was stirred for 4 hours. The crystals separating out were collected by filtration, washed with ethanol, and dried, whereby 12.7 g of N-(1-ethoxycarbonyl-3-oxo-3-phenylpropyl)-L-alanine (1S/1R ratio=95/5) was obtained.

In 110 ml of 1% (v/v) sulfuric acid-ethanol was dissolved 2.0 g of thus-obtained N-(1-ethoxycarbonyl-3-oxo-3-phenylpropyl)-L-alanine (1S/1R ratio=95/5), followed by addition of 0.5 g of 10% Pd/C, and catalytic reduction was carried out at room temperature under atmospheric pressure. After the reaction, the catalyst was removed by suction filtration, the filtrate was washed with ethanol and the obtained solution was concentrated. The concentrate was neutralized by adding water and sodium hydroxide and the crystals separating out were collected by filtration, washed with water, and dried to give 1.5 g of N-(1-ethoxycarbonyl-3-phenylpropyl)-L-alanine (1S/1R ratio=99/1). The mean particle diameter ($D_p^{50}$) of the crystals was 30 μm, the loose packing bulk specific gravity was about 0.3, and the flowability of the crystals was not satisfactory.

EXAMPLE 1

Five grams of N-(1(S)-ethoxycarbonyl-3-phenylpropyl)-L-alanine (purity 96.7%; impurities contained: N-(1(R)-ethoxycarbonyl-3-phenylpropyl)-L-alanine 0.8%, N-(1(S)-ethoxycarbonyl-3-cyclohexylpropyl)-L-alanine 0.84%, N-(1(S)-carboxy-3-phenylpropyl)-L-alanine 0.2%, N-(1(S)-ethoxycarbonyl-3-phenylpropyl)-L-alanine ethyl ester 0.5%, and ethyl phenylbutyrate 0.15%) was dissolved in 20 ml of a mixed solvent of ethanol and water (ethanol/water volume ratio 7) under warming (about 65° C.). The solution was cooled to 20° C. over 2 hours under stirring for crystallization (pH during crystallization 4 to 5). Then, under stirring, the system was further cooled to 10° C. and the resulting crystals were collected by filtration, washed with cold mixed solvent of ethanol and water (ethanol/water volume ratio 7), and dried in vacuo (40 to 60° C., overnight), whereupon dry crystals of N-(1(S)-ethoxycarbonyl-3-phenylpropyl)-L-alanine were obtained. Yield 84%, purity 100.0%. None of N-(1(R)-ethoxycarbonyl-3-phenylpropyl)-L-alanine, N-(1(S)-carboxy-3-phenylpropyl)-L-alanine, N-(1(S)-ethoxycarbonyl-3-phenylpropyl)-L-alanine ethyl ester, and ethyl phenylbutyrate were detected, and the N-(1(S)-ethoxycarbonyl-3-cyclohexylpropyl)-L-alanine content was 0.40% (removal rate 52%). The mean particle diameter ($D_p^{50}$) of the crystals was 170 μm, the loose packing bulk specific gravity was about 0.5, and the flowability of crystals was satisfactory.

EXAMPLE 2

Five grams of the same N-(1(S)-ethoxycarbonyl-3-phenylpropyl)-L-alanine as used in Example 1 was dissolved in 28 ml of a mixed solvent of isobutanol and water (isobutanol/water volume ratio 10) under warming (about 65° C.). The solution was cooled to 20° C. over 2 hours under stirring for crystallization (pH during crystallization 4 to 5). The crystals were collected by filtration, washed with a cold mixed solvent of isobutanol and water (isobutanol/water volume ratio 10), and dried in vacuo (40 to 60° C., overnight) to give dry crystals of N-(1(S)-ethoxycarbonyl-3-phenylpropyl)-L-alanine. Yield 81%, purity 99.9%. None of N-(1(R)-ethoxycarbonyl-3-phenylpropyl)-L-alanine, N-(1(S)-carboxy-3-phenylpropyl)-L-alanine, N-(1(S)-ethoxycarbonyl-3-phenylpropyl)-L-alanine ethyl ester, and ethyl phenylbutyrate were detected, and the N-(1(S)-ethoxycarbonyl-3-cyclohexylpropyl)-L-alanine content was 0.27% (removal rate 68%). The mean particle diameter ($D_p^{50}$) of crystals was 130 μm, the loose packing bulk specific gravity was about 0.5, and the flowability of crystals was satisfactory.

EXAMPLE 3

Five grams of the same N-(1(S)-ethoxycarbonyl-3-phenylpropyl)-L-alanine as used in Example 1 was dissolved in 20 ml of a mixed solvent of 1-propanol and water (1-propanol/water volume ratio 10) under warming (about 65° C.). The solution was cooled to 20° C. over 2 hours under stirring for crystallization (pH during crystallization 4 to 5). The crystals were collected by filtration, washed with a cold mixed solvent of 1-propanol and water (1-propanol/water volume ratio 10), and dried in vacuo (40 to 60° C., overnight) to give dry crystals of N-(1(S)-ethoxycarbonyl-3-phenylpropyl)-L-alanine. Yield 85%, purity 99.7%. None of N-(1-(R)-ethoxycarbonyl-3-phenylpropyl)-L-alanine, N-(1(S)-carboxy-3-phenylpropyl)-L-alanine, N-(1(S)-ethoxycarbonyl-3-phenylpropyl)-L-alanine ethyl ester, and ethyl phenylbutyrate were detected, and the N-(1(S)-ethoxycarbonyl-3-cyclohexylpropyl)-L-alanine content was 0.38% (removal rate 55%). The mean particle diameter ($D_p^{50}$) of the crystals was 120 μm, the loose packing bulk specific gravity was about 0.5, and the flowability of crystals was satisfactory.

Comparative Example 1

Five grams of N-(1(S)-ethoxycarbonyl-3-phenylpropyl)-L-alanine (as an impurity, 0.84% of N-(1(S)-ethoxycarbonyl-3-cyclohexylpropyl)-L-alanine was contained) was dissolved in 50 ml of isobutanol under warming (about 65° C.). When the solution was cooled to 20° C. over 2 hours under stirring for crystallization, it solidified to form cakes. The crystals were collected by filtration, washed with cold isobutanol, and dried in vacuo (40 to 60° C., overnight) to give dry crystals of N-(1(S)-ethoxycarbonyl-3-phenylpropyl)-L-alanine. Yield 63%, the N-(1(S)-ethoxycarbonyl-3-cyclohexylpropyl)-L-alanine content was 0.40% (removal rate 52%).

Comparative Example 2

Five grams of N-(1(S)-ethoxycarbonyl-3-phenylpropyl)-L-alanine (as an impurity, 0.84% of N-(1(S)-ethoxycarbonyl-3-cyclohexylpropyl)-L-alanine was contained) was dissolved in 30 ml of ethanol under warming (about 65° C.). When the solution was cooled to 20° C. over 2 hours under stirring for crystallization, it solidified to form cakes. The crystals were collected by filtration, washed with cold ethanol, and dried in vacuo (40 to 60° C., overnight) to give dry crystals of N-(1(S)-ethoxycarbonyl-3-phenylpropyl)-L-alanine. Yield 67%, the N-(1(S)-ethoxycarbonyl-3-cyclohexylpropyl)-L-alanine content was 0.47% (removal rate 44%).

Comparative Example 3

Five grams of N-(1(S)-ethoxycarbonyl-3-phenylpropyl)-L-alanine (as an impurity, 0.84% of N-(1(S)-ethoxycarbonyl-3-cyclohexylpropyl)-L-alanine was contained) was dissolved in 32 ml of a mixed solvent of ethanol and cyclohexane (ethanol/cyclohexane volume ratio 2) under warming (about 65° C.). The solution was cooled to 20° C. over 2 hours under stirring for crystallization. The crystals were collected by filtration, washed with a cold mixed solvent of ethanol and cyclohexane (ethanol/cyclohexane volume ratio 2), and dried in vacuo (40 to 60° C., overnight) to give dry crystals of N-(1(S)-ethoxycarbonyl-3-phenylpropyl)-L-alanine. Yield 70%. The N-(1(S)-ethoxycarbonyl-3-cyclohexylpropyl)-L-alanine content was 0.48% (removal rate 43%).

EXAMPLE 4

Thirty grams of N-(1(S)-ethoxycarbonyl-3-phenylpropyl)-L-alanine (purity 96.4%; impurities contained: N-(1(R)-ethoxycarbonyl-3-phenylpropyl)-L-alanine 0.10% and N-(1(S)-ethoxycarbonyl-3-cyclohexylpropyl)-L-alanine 0.11%) was dissolved in 100 ml of a mixed solvent of ethanol and water (ethanol/water volume ratio 2.96) under warming (about 65° C.). The solution was treated with 3 g of 50% hydrous active charcoal for 1 hour, the mixture was then filtered when hot, and washed with 10 ml of a mixed solvent of ethanol and water (ethanol/water volume ratio 16.9). The resulting solution was rapidly cooled to 20° C. under vigorous stirring (0.3 kW/m$^3$) (cooling speed 40° C./hr) and further stirred for 2 hours (pH during crystallization 4 to 5). The crystals were collected by filtration, washed with a cold mixed solvent of ethanol and water (ethanol/water volume ratio 16.9), and dried in vacuo to give dry crystals of N-(1(S)-ethoxycarbonyl-3-phenylpropyl)-L-alanine. Yield 85%; N-(1(R)-ethoxycarbonyl-3-phenylpropyl)-L-alanine was not detected and the N-(1(S)-ethoxycarbonyl-3-cyclohexylpropyl)-L-alanine content was 0.050% (removal rate 55%).

EXAMPLE 5

The procedure of Example 4 was repeated except that the crystallization was carried out at a cooling speed of 10° C./hour. Yield 85%; N-(1(R)-ethoxycarbonyl-3-phenylpropyl)-L-alanine was not detected and the N-(1(S)-ethoxycarbonyl-3-cyclohexylpropyl)-L-alanine content was 0.044% (removal rate 60%).

EXAMPLE 6

The procedure of Example 4 was repeated except that the crystallization was carried out at a cooling speed of 5° C./hour. Yield 85%; N-(1(R)-ethoxycarbonyl-3-phenylpropyl)-L-alanine was not detected and the N-(1(S)-ethoxycarbonyl-3-cyclohexylpropyl)-L-alanine content was 0.035% (removal rate 68%).

EXAMPLE 7

Five grams of N-(1(S)-ethoxycarbonyl-3-phenylpropyl)-L-alanine (purity 96.7%; impurities contained: N-(1(R)-ethoxycarbonyl-3-phenylpropyl)-L-alanine 0.8%, N-(1(S)-ethoxycarbonyl-3-cyclohexylpropyl)-L-alanine 0.84%, N-(1(S)-carboxy-3-phenylpropyl)-L-alanine 0.2%, N-(1(S)-ethoxycarbonyl-3-phenylpropyl)-L-alanine ethyl ester 0.5%, and ethyl phenylbutyrate 0.15%) was dissolved in 17 ml of a mixed solvent of ethanol and water (ethanol/water volume ratio 2.3) under warming (about 65° C.). This solution was treated with 1 g of 50% hydrous active charcoal for 10 minutes, the mixture was then filtered when hot, and washed with 3 ml of the mixed solvent of ethanol and water (ethanol/water volume ratio 2.3). The filtrate thus obtained was cooled to 20° C. over 2 hours under stirring (0.2 kW/m$^3$) for crystallization (pH during crystallization 4 to 5). The slurry was further cooled to 10° C. under stirring (0.2 kW/m$^3$), after which the crystals were collected by filtration, washed with a cold mixed solvent of ethanol and water (ethanol/water volume ratio 16.9), and dried in vacuo (40 to 60° C., overnight) to give dry crystals of N-(1(S)-ethoxycarbonyl-3-phenylpropyl)-L-alanine. Yield 83%, purity 99.9%. None of N-(1(R)-ethoxycarbonyl-3-phenylpropyl)-L-alanine, N-(1(S)-carboxy-3-phenylpropyl)-L-alanine, N-(1(S)-ethoxycarbonyl-3-phenylpropyl)-L-alanine ethyl ester, and ethyl phenylbutyrate were detected, the N-(1(S)-ethoxycarbonyl-3-cyclohexylpropyl)-L-alanine content was 0.40% (removal rate 52%), and the iron content was 0.5 ppm. The mean particle diameter ($D_p^{50}$) of the crystals was 160 μm, the loose packing bulk specific gravity was about 0.5, and the flowability of crystals was satisfactory.

Comparative Example 4

Five grams of the same N-(1(S)-ethoxycarbonyl-3-phenylpropyl)-L-alanine as used in Example 7 was added to 55 ml of water and dissolved by adding 1.9 ml of concentrated hydrochloric acid. This solution was treated with 1 g of 50% hydrous active charcoal for 10 minutes, and the mixture was then filtered and washed with 5 ml of water. To this filtrate was added 1 ml of 30% aqueous solution of sodium hydroxide over 1 hour at 25 to 28° C. under stirring (0.2 kW/m$^3$) to adjust the pH of the solution to 4.7. The solution was stirred at 22° C. for 1 hour, and the crystals were collected by filtration, washed with 5 ml of water, and dried in vacuo (40 to 60° C., overnight) to give dry crystals of N-(1(S)-ethoxycarbonyl-3-phenylpropyl)-L-alanine. Yield 86%, purity 99.1%; neither N-(1(S)-carboxy-3-phenylpropyl)-L-alanine nor ethyl phenylbutyrate was detected. The N-(1(R)-ethoxycarbonyl-3-phenylpropyl)-L-alanine content was 0.1%, the N-(1(S)-ethoxycarbonyl-3-phenylpropyl)-L-alanine ethyl ester content was 0.2%, the N-(1(S)-ethoxycarbonyl-3-cyclohexylpropyl)-L-alanine content was 0.84% (removal rate 0%), and the iron content was 30 ppm. The mean particle diameter ($D_p^{50}$) of the crystals was 70 μm, the loose packing bulk specific gravity was about 0.3, and the flowability of crystals was not as good as desired.

In the purification method according to each of Examples as shown above, N-(1(S)-ethoxycarbonyl-3-phenylpropyl)-L-alanine of high quality, namely of high purity having favorable powder characteristics (especially, the mean particle diameter was within a favorable range of 100 to 1000 μm, the loose packing bulk specific gravity was within a favorable range of 0.4 to 0.7 and the flowability of crystals was satisfactory) could be purified and obtained in good yield with high productivity.

Reference Example 1

The powder characteristics of the crystals obtained in the same manner as in Example 7 were studied using Hosokawa Micron's powder tester. The results are shown below.
Apparent specific gravity, loose: 0.47
Apparent specific gravity, packed: 0.55
Degree of compaction, %: 15
Degree of compaction, index: 20
Angle of repose, degree: 43
Angle of repose, index: 16
Spatula angle, degree: 46
Spatula angle, index: 17
Degree of uniformity, unit: 2.1
Degree of uniformity, index: 23
Flowability index: 76
Degree of flowability: fairly good It was found from the above results that the powder characteristics of the above crystals were excellent.

Reference Example 2

The powder characteristics of the crystals obtained in the same manner as in Comparative Example 4 were studied using Hosokawa Micron's powder tester. The results are shown below.
Apparent specific gravity, loose: 0.24
Apparent specific gravity, packed: 0.39
Degree of compaction, %: 39
Degree of compaction, index: 2
Angle of repose, degree: 50
Angle of repose, index: 12

Spatula angle, degree: 66
Spatula angle, index: 12
Degree of uniformity, unit: 1.6
Degree of uniformity, index: 24
Flowability index: 50
Degree of flowability: not as good as desired It was found from the results shown above that the powder characteristics of the above crystals were inferior comparing to Reference Example 1.

Reference Example 3

One-hundred milliliters each of mixed solvents of ethanol and water in predetermined volume ratios were respectively adjusted to predetermined temperatures and each solvent was added until a pure product of N-(1(S)-ethoxycarbonyl-3-phenylpropyl)-L-alanine was no longer dissolved. After 30 minutes of standing, the supernatant was taken and the solubility (weight %) was determined according to the weight after concentration to dryness/the weight of the solution. The results are shown in Table 1.

TABLE 1

| | | Ethanol/water volume ratio and solubility (weight %) | | | | | | |
|---|---|---|---|---|---|---|---|---|
| Volume ratio | | 0.43 | 1.00 | 2.33 | 4.00 | 5.67 | 15.7 | 249 |
| Solubility | 65° C. | 9 | 21 | 42 | 45 | 42 | 26 | 17 |
| | 20° C. | — | 3 | 4 | 5 | 5 | 4 | 3 |
| | 10° C. | 1 | 2 | 3 | 4 | 3 | 3 | 2 |

As shown in the above, when ethanol/water volume ratio is 1 to 20, the solubility is highly dependent on the temperature, hence improved yield and productivity (crystallization concentration) are expected by using the mixed solvent as the crystallization solvent.

INDUSTRIAL APPLICABILITY

By the purification method of the invention, N-(1(S)-ethoxycarbonyl-3-phenylpropyl)-L-alanine of high quality, namely of high purity and having favorable powder characteristics, can be purified and obtained in good yield with high productivity.

The invention claimed is:

1. A purification method of N-(1(S)-ethoxycarbonyl-3-phenylpropyl)-L-alanine represented by the formula (1)

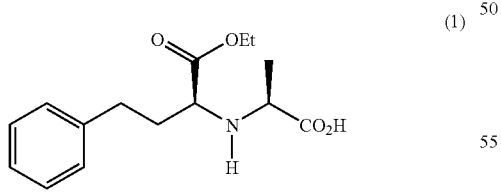

which comprises crystallizing impurity-contaminated N-(1(S)-ethoxycarbonyl-3-phenylpropyl)-L-alanine from a mixed solvent of alcohol and water in a volume ratio of alcohol/water being 1/1 to 20/1 to remove a contaminating impurity into a mother liquor and give crystals of N-(1(S)-ethoxycarbonyl-3-phenylpropyl)-L-alanine,
said alcohol being a monohydric alcohol of 1 to 12 carbon atoms.

2. The purification method according to claim 1 wherein the contaminating impurity is at least one compound selected from the group consisting of N-(1(R)-ethoxycarbonyl-3-phenylpropyl)-L-alanine represented by the following formula (2),

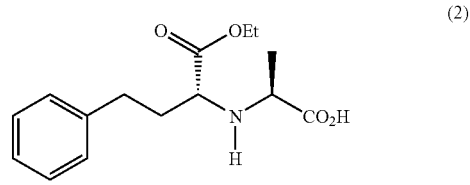

N-(1(S)-ethoxycarbonyl-3-phenylpropyl)-D-alanine represented by the following formula (3),

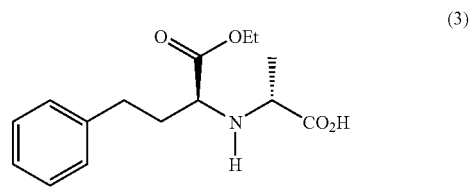

N-(1(R)-ethoxycarbonyl-3-phenylpropyl)-D-alanine represented by the following formula (4),

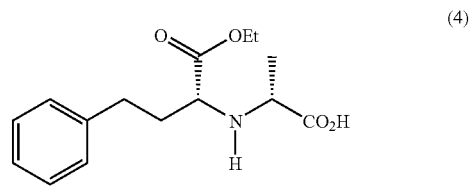

N-(1(S)-ethoxycarbonyl-3-cyclohexylpropyl)-L-alanine represented by the following formula (5),

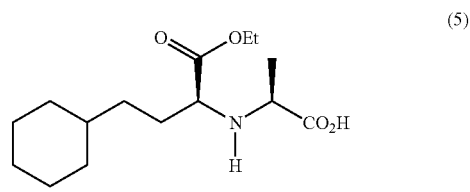

N-(1(S)-carboxy-3-phenylpropyl)-L-alanine represented by the following formula (6),

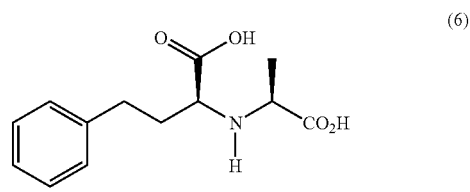

N-(1(S)-ethoxycarbonyl-3-phenylpropyl)-L-alanine ester of the following formula (7)

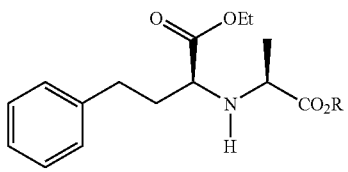

(7)

in the formula, R represents an alkyl group or an aralkyl group, and ethyl phenylbutyrate.

3. The purification method according to claim 1 wherein the crystallization is carried out under forced fluidity with a condition of not less than 0.1 kW/m3.

4. The purification method according to claim 1 wherein in the crystallization is carried out at a temperature of not lower than 20° C.

5. The purification method according to claim 1 wherein the crystallization is carried out at a crystallizing speed of not more than 50% of a total crystal output/hour.

6. The purification method according to claim 1 wherein the crystallization is carried out at pH 3 to 6.

7. The purification method according to claim 1 wherein the crystallization is carried out by at least one of crystallization by cooling and crystallization by concentration.

8. The purification method according to claim 7 wherein the crystallization is carried out by crystallization by cooling.

9. The purification method according to claim 8 wherein the cooling speed for the crystallization by cooling is not more than 40° C./hour.

10. The purification method to claim 1 wherein the alcohol is a monohydric alcohol of 1 to 8 carbon atoms.

11. The purification method according to claim 10 wherein the alcohol is a monohydric alcohol of 1 to 4 carbon atoms.

12. The purification method according to claim 11 wherein the alcohol is ethanol.

13. The purification method according to claim 12 wherein the ethanol is denatured with at least one denaturing agent selected from the group consisting of ethyl acetate, methyl isobutyl ketone, aliphatic hydrocarbons and aromatic hydrocarbons.

14. The purification method according to claim 1 wherein a treatment with an active charcoal is carried out prior to the crystallization.

15. The purification method according to claim 2 where in the crystallization is carried out under forced fluidity with a condition of not less than 0.1 kW/m3.

16. The purification method according to claim 3 where in the crystallization is carried out at a temperature of not lower than 20° C.

17. The purification method according to claim 4 wherein the crystallization is carried out at a crystallizing speed of not more than 50% of a total crystal output/hour.

18. The purification method according to claim 5 wherein the crystallization is carried out at pH 3 to 6.

19. The purification method according to claim 6 wherein the crystallization is carried out by at least one of crystallization by cooling and crystallization by concentration.

20. The purification method according to claim 1, wherein the volume ratio of alcohol/water is 1.5 to 20.

21. The purification method according to claim 20, wherein the volume ratio of alcohol/water is 2 to 20.

22. The purification method according to claim 1, which is a method for reducing N-1(S)-ethoxycarbonyl-3-cyclohexylpropyl-L-alanine content to not more than 0.47% through a crystallization process.

* * * * *